US008391973B2

(12) United States Patent
Nikolski et al.

(10) Patent No.: US 8,391,973 B2
(45) Date of Patent: Mar. 5, 2013

(54) APPARATUS AND METHOD FOR NON-INVASIVE INDUCTION OF VENTRICULAR FIBRILLATION

(75) Inventors: Vladimir P. Nikolski, Blaine, MN (US); William J. Havel, Maple Grove, MN (US); Joseph L. Sullivan, Kirkland, WA (US); Daniel W. Piraino, Seattle, WA (US); Eric R. Williams, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1196 days.

(21) Appl. No.: 11/969,663

(22) Filed: Jan. 4, 2008

(65) Prior Publication Data

US 2009/0177242 A1    Jul. 9, 2009

(51) Int. Cl.
    A61N 1/39    (2006.01)
(52) U.S. Cl. ..................... 607/4; 607/5; 607/9
(58) Field of Classification Search .......... 607/5, 6, 607/7, 8, 20, 21, 32, 4, 9
    See application file for complete search history.

(56) References Cited

U.S. PATENT DOCUMENTS

| 4,316,472 | A | * | 2/1982 | Mirowski et al. | 607/9 |
|---|---|---|---|---|---|
| 5,129,392 | A | | 7/1992 | Bardy et al. | |
| 5,184,616 | A | | 2/1993 | Weiss | |
| 5,346,506 | A | | 9/1994 | Mower et al. | |
| 5,554,174 | A | * | 9/1996 | Causey, III | 607/5 |
| 5,591,209 | A | * | 1/1997 | Kroll | 607/5 |
| 5,609,618 | A | | 3/1997 | Archer | |
| 5,709,711 | A | * | 1/1998 | Fain | 607/8 |
| 7,096,064 | B2 | * | 8/2006 | Deno et al. | 607/9 |
| 2002/0026141 | A1 | * | 2/2002 | Houben et al. | 604/66 |
| 2009/0099618 | A1 | * | 4/2009 | Rousso et al. | 607/25 |

OTHER PUBLICATIONS

Sharma AD, et al. "Shock on T versus direct current voltage for induction of ventricular fibrillation: A randomized prospective comparison." Pacing Clin. Electrophsyiol., Jan. 2004; pp. 89-94, 27(1).
Mazer CE et al. "Transcutaneous T wave shock: A universal method for ventricular fibrillation induction" Pacing Clin Electrophysiol. Dec. 1997, pp. 2930-2935, 20(12 Pt 1).
Sander WE et al. "Ventricular fibrillation induction using nonsynchronized low energy external shock during rapid ventirucular pacing: method of induction when fibrillation mode of ICD fails." Pacing Clin Electrophysiol. Apr. 1996. pp. 431-436. 19(4 Pt 1).
Hauer B et al. "The T-wave shock: a new reliable method for induction of ventricular fibrillation in ICD testing." Z Kardiol. Apr. 1995, pp. 284-288. 84(4).
Rosenfeld LE et al. "Ventricular tachycardia induction: comparison of triple extrastimuli with an abrupt change in ventricular drive cycle length". Am Heart J. May 1986. pp. 868-874. 111(5).

* cited by examiner

*Primary Examiner* — Nicole F Lavert
*Assistant Examiner* — Pamela M Bays
(74) *Attorney, Agent, or Firm* — Michael C. Soldner

(57) ABSTRACT

An apparatus and method for delivering an external shock pulse receive pacing pulses generated by a first device and a shock pulse generated by a second device. An output of the apparatus is coupled to patient electrodes and the apparatus controls delivery of the received pacing pulses to the output and delivery of the received shock pulse to the output. A control module, pacing control and shock control included in the apparatus cooperatively control delivery of the received shock pulse to the output at a predetermined delay after one of the received pacing pulses.

12 Claims, 3 Drawing Sheets

APPARATUS AND METHOD FOR NON-INVASIVE INDUCTION OF VENTRICULAR FIBRILLATION

TECHNICAL FIELD

The invention relates generally to medical devices and, in particular, to a system and method for controlling delivery of an externally generated shock pulse.

BACKGROUND

Delivery of a shock pulse during the vulnerable period of the cardiac cycle can induce fibrillation, providing the shock energy is greater than a patient-specific minimum value and less than a patient-specific maximum value. Such a shock pulse is generally referred to as a "T-shock" or "T-wave shock" because the time of the vulnerable period during the cardiac cycle generally corresponds to the T-wave of the ECG signal.

Patients receiving an implantable cardioverter defibrillator (ICD) typically undergo defibrillation threshold testing in order to ensure a reasonable certainty of successful defibrillation using shock pulse energies corresponding to the output capacity of the ICD. The DFT has been determined by inducing fibrillation through delivery of a shock during the T-wave, then delivering defibrillation shocks to verify successful defibrillation at shock energies at least a safety margin below the maximum ICD output. ICDs are typically connected to intracardiac leads which are used to deliver a sequence of pacing pulses and deliver a T-shock. A sequence of pacing pulses, for example, six to eight pacing pulses, is delivered in order to facilitate delivery of a shock pulse synchronized with the T-wave during a stable cardiac rhythm. The T-wave shock is synchronized to the T-wave for inducing fibrillation by delivering the shock at a predetermined shock interval following the last pacing pulse. If fibrillation is induced, the ICD will detect the fibrillation and deliver a test defibrillation pulse to terminate the induced fibrillation.

Subcutaneous ICD systems are emerging which do not utilize intracardiac leads for sensing cardiac signals and delivering defibrillation shock pulses. Such systems, however, may not include fibrillation induction capabilities. As such, a need exists to induce fibrillation without the use of intra-cardiac leads to allow defibrillation threshold testing, for example, during subcutaneous ICD system implantation.

DETAILED DESCRIPTION

Figure 1:
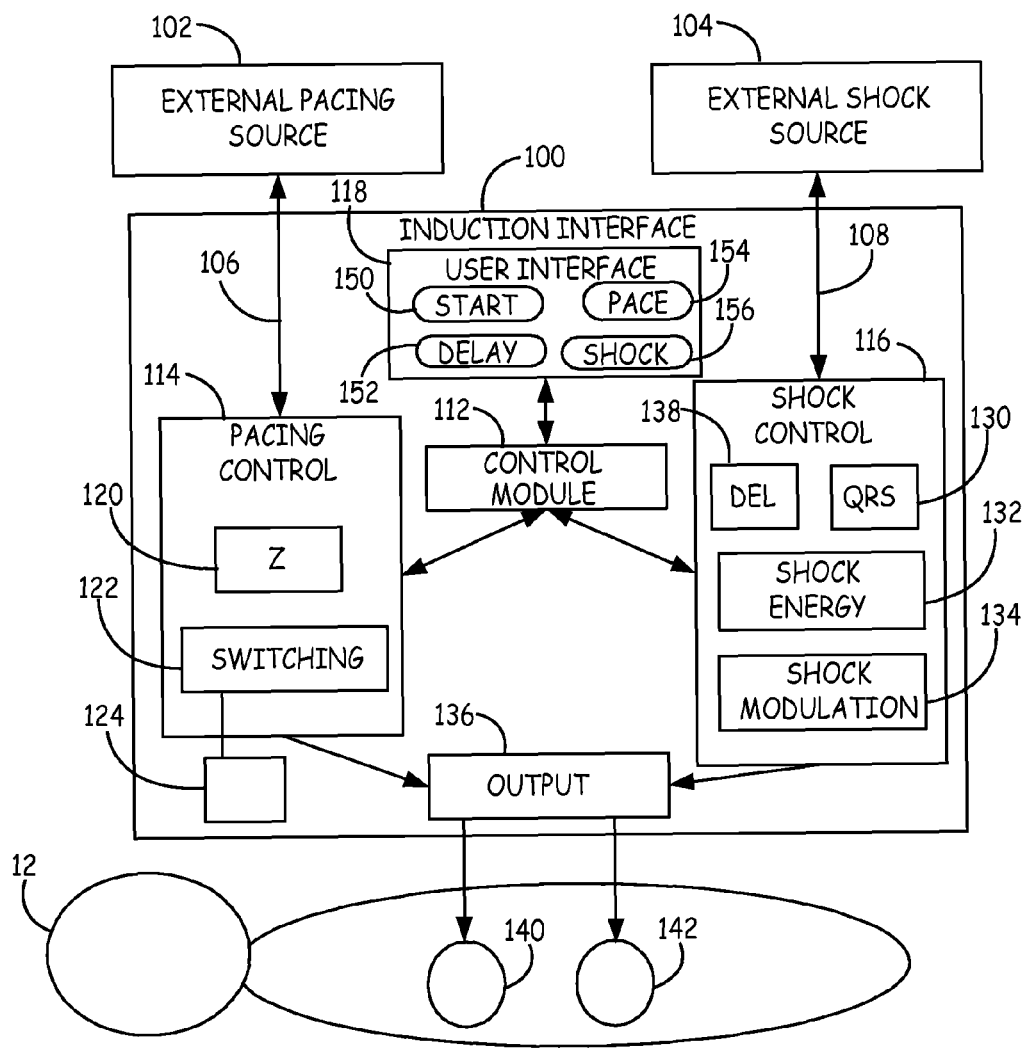
FIG. 1 is a functional block diagram of a system for external induction of ventricular fibrillation.

In the following description, references are made to illustrative embodiments for carrying out the invention. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 is a functional block diagram of a system for external induction of ventricular fibrillation. The system 10 includes a fibrillation induction interface 100 coupled to an external pacing source 102 and an external shock source 104. Induction interface 100 is further coupled to electrodes 140 and 142 for delivering pacing pulses and shock pulses to a patient 12. System 10 is intended for use as a non-invasive system for inducing fibrillation, and as such electrodes 140 and 142 are embodied as surface electrodes adapted to be positioned on the skin of patient 12. However, it is recognized that in various embodiments of the invention, portions of system 10 may be implanted in a patient 12. For example, electrodes 140 and 142 may be positioned subcutaneously or submuscularly.

External pacing source 102 and external shock source may be embodied as separate units or included in one unit including both pacing pulse generation and shock pulse generation capabilities. External pacing source 102 is provided having the capabilities for generating pacing pulses that are of sufficient energy to capture the heart using electrodes 140 and 142. External shock source 104 is provided having the capability for generating shock pulses that are sufficient to induce fibrillation using electrodes 140 and 142. It is contemplated that external pacing source 102 and external shock source 104 are provided as commercially available external defibrillators in one embodiment, for example as LifePak® 12, available from Medtronic, Inc., Minneapolis, Minn., USA.

In one embodiment, external shock source 104 is implemented as an external defibrillator capable of sensing a patient's ECG signal via electrodes directly coupled to shock source 104 and deliver a defibrillation shock pulse to the patient electrodes, synchronized to the patient's R-wave during fibrillation. For the purposes of inducing fibrillation according to embodiments of the present invention, however, external shock source 104 is coupled indirectly to electrodes 140 and 142 via induction interface 100.

Induction interface 100 is used to interface the external pacing source 102 and the external shock source 104 with the patient 12 during defibrillation threshold testing. Induction interface 100 functions cooperatively with external pacing source 102 and external shock source 104 to non-invasively deliver a T-wave shock to patient 12 using electrodes 140 and 142. Induction interface 100 includes a control module 112, a pacing control 114 and a shock control 116. The control module 112 in cooperation with pacing control 114 and shock control 116 control the delivery of a pacing pulse series and a T-wave shock to patient 12 using electrodes 140 and 142.

Induction interface 100 includes an input line 106 for receiving pacing pulses generated by external pacing source 102 and provide the received pacing pulses to pacing control 114. Input line 106 may be embodied as an input/output line, for example as a serial bus, which allows signals to be transferred bidirectionally between external pacing source 102 and induction interface 100.

Pacing pulses generated by external pacing source 102 are received by pacing control 114 which connects input 106 to a pacing load 120. Pacing load 120 is applied to input 106 coupled to pacing source 102 such that pacing source 102 "sees" an artificial impedance that corresponds to a pacing lead impedance that would typically be present when pacing source 102 is directly coupled to electrodes 140 and 142 positioned on patient 12. In some embodiments, pacing source 102 may require a pacing load to be connected to pacing source 102 in order to actually generate pacing pulses. Induction interface 100 provides the necessary impedance load 120 upon coupling to pacing source 102. In response to "seeing" the artificial impedance load 120 and being enabled to operate in a pacing mode, external pacing source 102 generates pacing pulses that are received by induction interface 100.

External pacing source 102 may be manually enabled directly by a user to start generating pacing pulses, having a desired pulse energy and at a desired rate. Alternatively, control module 112 and/or pacing control 114 may be configured to signal external pacing source 102 to initiate pacing pulses. User interface 118 may be configured to allow a user to select a pacing pulse rate and pulse energy or a default rate and pulse energy may be stored in control module 112 or pacing control 114. Once pacing pulses are being received by pacing control 114, the pacing pulses may be initially withheld from patient 12. In other words, the pacing pulses will be dissipated within induction interface 100. The delivery of pacing pulses to an output interface 136 coupled to electrodes 140 and 142 is controlled by switching circuitry 122. When received pacing pulses are not delivered to the patient, switching circuitry 122 disconnects pacing control 114 from output 136 and passes received pacing pulses to the dissipative circuitry 124. Dissipative circuitry 124 may be embodied as a passive resistor or other dissipating component(s).

The artificial impedance load 120 is disconnected from the input line 106 when the pacing pulses are passed to the electrodes. The external pacing source 102 sees the real impedance of electrodes 140 and 142 when the pacing pulses are actually delivered to the patient because the impedance 120 is no longer connected. The artificial impedance load 120 may be connected to external shock source 104 to promote proper functionality of the shock source 104 if the shock source 104 is disconnected from the patient during the delivery of the pacing pulses.

The external shock source 104 is coupled to shock control 116 via input/output line 108 to allow shock pulses generated by shock source 104 to be passed to patient 12 via interface 100 and electrodes 140 and 142. Input/output line 108 may be embodied as a serial bus, which allows signals to be transferred bidirectionally between external shock source 104 and induction interface 100.

External shock source 104 may be manually enabled to initiate capacitor charging for generating a shock pulse. Shock delivery parameters may additionally be set manually. In particular, a shock delivery mode is set as a synchronized shock delivery such that the shock is synchronized with a QRS signal. Other shock delivery parameters that may be set manually include the shock energy and the shock waveform. Alternatively, control module 112 and/or shock control 116 may be configured to send a charge command via input/output line 108 to trigger external shock source 104 to initiate capacitor charging. The charge command may further include charge energy and other shock control parameter data for instructing external shock source 104 to generate a shock according to the command parameters. User interface 118 may be used to enter shock control parameters such as shock energy, shock waveform and a desired shock delay relative to a QRS signal. Default shock control parameters may be stored by control module 112 or shock control 116.

Shock control 116 includes a QRS signal generator 130 for generating a simulated QRS signal that is provided to shock source 104 via input/output line 108. The simulated QRS signal is provided to shock source 104 as a signal for synchronizing delivery of a shock pulse. QRS signal generator 130 receives a predetermined delay 138 which maybe set by a user using user interface 118. The delay 138 may alternatively be implemented as a default value or selection of default values stored by shock control 116 and selectable by a user using user interface 118.

Shock control 116 may include shock energy control 132 for adjusting a received shock pulse to a selected shock energy. The selected shock energy may be a default value stored by shock control module 116 or selected by a user using user interface 118. Shock control 116 may include circuitry for adjusting the energy of a received shock pulse, for example by truncating, prolonging, amplifying or dampening the shock pulse, to a selected shock energy. Alternatively, shock control 115 may store a selected shock energy parameter to be delivered to external shock source 103 with a charge command via input/output line 108.

Shock control 116 further includes shock modulation circuitry 134 for modulating the shock waveform received from external shock source 104. Shock modulation circuitry 134 may include a rectifier to convert a biphasic shock pulse to a monophasic shock pulse. Shock modulation circuitry 134 may further include circuitry for prolonging the pulse duration of a shock pulse. A shock pulse received by shock control 116 and modulated by circuitry 134 is passed to output interface 136 and patient electrodes 140 and 142.

User interface 118 may be implemented as a "start" button to initiate a fibrillation induction procedure. By pressing the start button 150, induction interface 100 generates the QRS signals provided to external shock source 104 and connects external pacing source 102 to the patient to deliver pacing pulses at an overdrive rate to ensure a stable heart rate for synchronizing a shock pulse. The start button 150 may also trigger a charge command issued to external shock source 104. User interface may further include a "cancel" button, which may be a dedicated button or start button 150 may perform a dual function of starting or canceling an induction procedure. The cancel button may be used by a user to cancel the induction operation, for example when pacing pulses are not successfully delivered to capture the patient's heart.

User interface 118 may further include user-selectable parameter inputs such as a delay selector 152 for selecting the predetermined delay between a pacing pulse and a delivered shock pulse. The predetermined delay is used by induction interface 100 to set the delay between a generated QRS signal and a received pacing pulse for causing external shock source 104 to deliver a shock pulse during the patient's T-wave, synchronized to the artificial QRS signal. User-interface 118 may further include a shock energy selector 154 for setting a shock pulse energy to be stored by shock energy control 132 or other shock pulse control parameter. User interface 118 may further include a pacing rate and/or pacing pulse energy selector 156 for storage by pacing control 106. The shock energy and pacing rate and pulse energy selected using user interface 118 may be transferred to external shock source 104 and external pacing source 102 via lines 108 and 106, respectively, for controlling the shock delivery and pacing delivery. Alternatively, the user-selected shock and pacing control parameters may be used by induction interface 100 to modify the received shock pulse and received pacing pulses to conform to user selected values.

Figure 2:
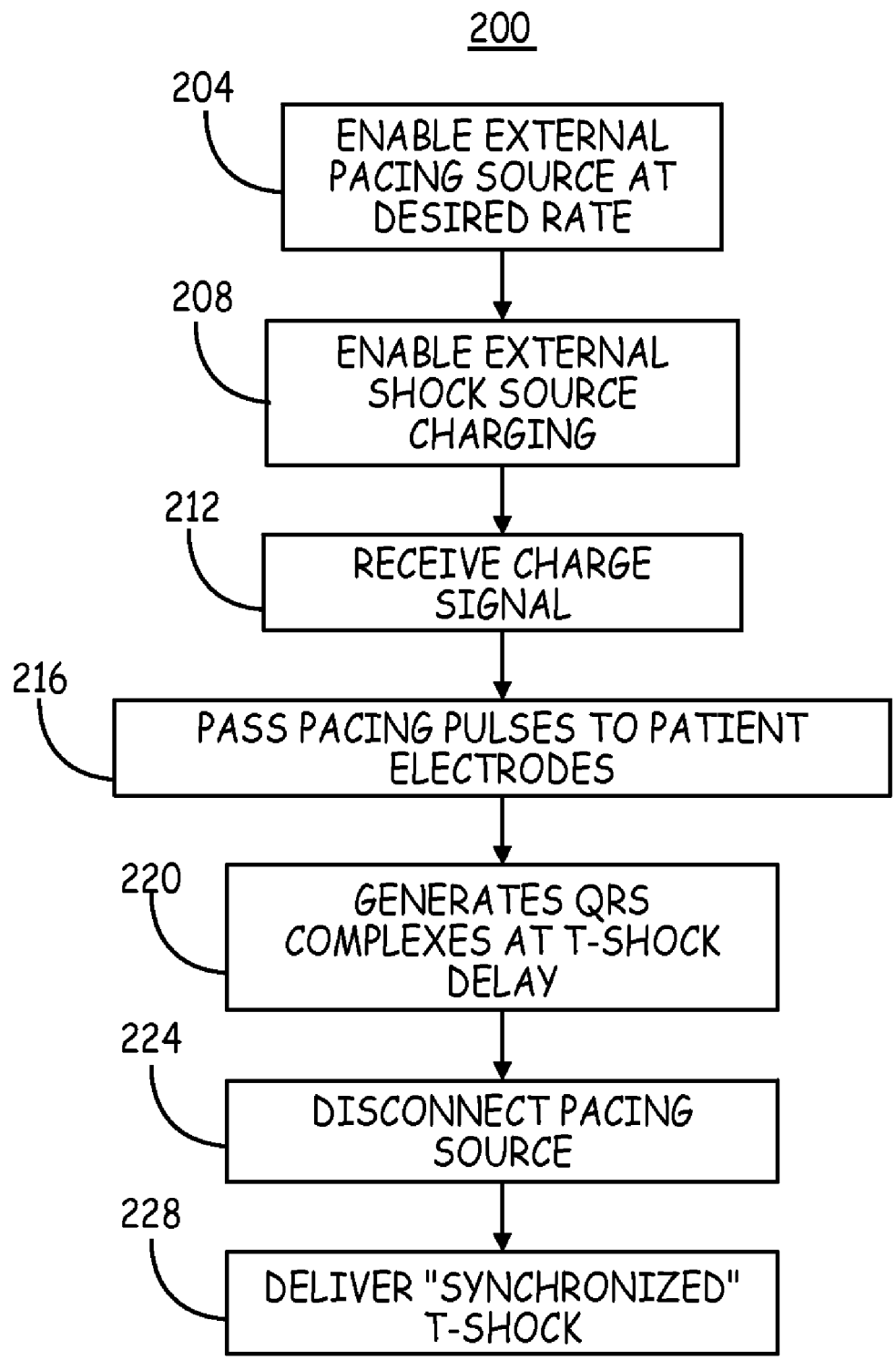
FIG. 2 is a flow chart of a method for controlling the delivery of an externally applied T-wave shock for inducing fibrillation using an external induction interface coupled to external pacing and shock sources as shown in FIG. 1.

FIG. 2 is a flow chart of a method for controlling the delivery of an externally applied T-wave shock for inducing fibrillation using an external induction interface coupled to external pacing and shock sources as shown in FIG. 1. Flow chart 200 is intended to illustrate the functional operation of the device, and should not be construed as reflective of a specific form of software or hardware necessary to practice the invention. It is believed that the particular form of software and hardware will be determined by the particular system architecture employed in the external pacing source, external shock source and interface and by the pacing and shock delivery methodologies employed by external sources. Providing software, firmware and hardware to accomplish the present invention, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 204, the external pacing source is enabled for delivering pacing pulses at a desired pulse energy and desired pacing rate. The external pacing source may be manually enabled directly by a user. Alternatively, a user may initiate method 200 using a user interface 118 included in the induction interface 100. In response to user initiation, the induction interface 100 sends a command to the external pacing source to initiate pacing pulse generation. The induction interface further enables pacing pulse generation by connecting the input received from the external pacing source to an artificial impedance load. The pacing pulses initially received from the external pacing source are dissipated by the induction interface and not passed to the patient until the external shock source has completed, or nearly completed, capacitor charging required for delivering a shock pulse.

At block 208, the external shock source is enable to initiate charging of capacitors for generating a shock pulse. As discussed previously, the external shock source may be manually enabled directly by a user or may be enabled by the induction interface 100. For example, in one embodiment, a user may initiate a fibrillation induction by pressing an "induce fibrillation" button. In response to this command, the induction interface will generate a command to the external pacing source to initiate pacing pulses and couple the pacing source to the artificial impedance load and generate a command to the external shock source to initiate capacitor charging.

At block 212, the induction interface 100 receives a charge signal indicating the external shock source 104 has completed or nearly completed charging. The charge signal may be automatically generated by the external shock source on input/output line 108 or may be provided by a user observing the external shock source 104 and using the user interface 118. In response to receiving a charge signal indicating that capacitor charging has been completed or has reached a threshold level, the induction interface 100 allows the pacing pulses received from the external pacing source 102 to be passed to the patient at block 216. The artificial impedance load 120 is disconnected from the external pacing source and the pacing pulses are transferred directly to electrodes coupled to the patients.

At block 220, the induction interface 100 generates artificial QRS signals, i.e. electrical signals that simulate physiological QRS signals. Each artificial QRS signal is transferred from induction interface 100 to external shock source 104 at a predetermined time delay following a pacing pulse received from external pacing source 102. The predetermined time delay corresponds to a desired T-shock delay. The desired T-shock delay may be a default setting or user-entered and corresponds to a time interval between a delivered pacing pulse and the expected occurrence of the patient's T-wave.

External shock source 104 recognizes the artificial QRS signals for use in synchronizing a shock pulse. External shock source 104 is configured to deliver a defibrillation shock pulse synchronized to a sensed QRS complex during a synchronized shock mode of operation. Induction interface 100 provides an artificial QRS complex to the external shock source 104 to cause a shock pulse synchronized to the artificial QRS complex to be delivered at a T-shock interval following a pacing pulse. The QRS complex is synchronized to the patient T-wave thus controlling shock pulse delivery during the T-wave for fibrillation induction.

Induction interface 100 disconnects the external pacing source 102 from the patient electrodes 140 and 142 at block 224 to prevent damage to external pacing source during shock delivery. A T-shock is delivered at block 228 by passing a shock pulse received from external shock source 104 to the patient electrodes synchronized to the artificial QRS signal occurring at predetermined delay following the last delivered pacing pulse. Induction interface 100 may be configured to pass a desired number of pacing pulses that corresponds to a required number of "sensed" QRS signals used by external shock source 104 for synchronizing a shock pulse then disconnect the pacing source 102 and pass the shock pulse to the patient electrodes. Disconnection of the pacing source may occur based on a specified number of delivered pulses, a predetermined time delay or other timing mechanism.

Figure 3:
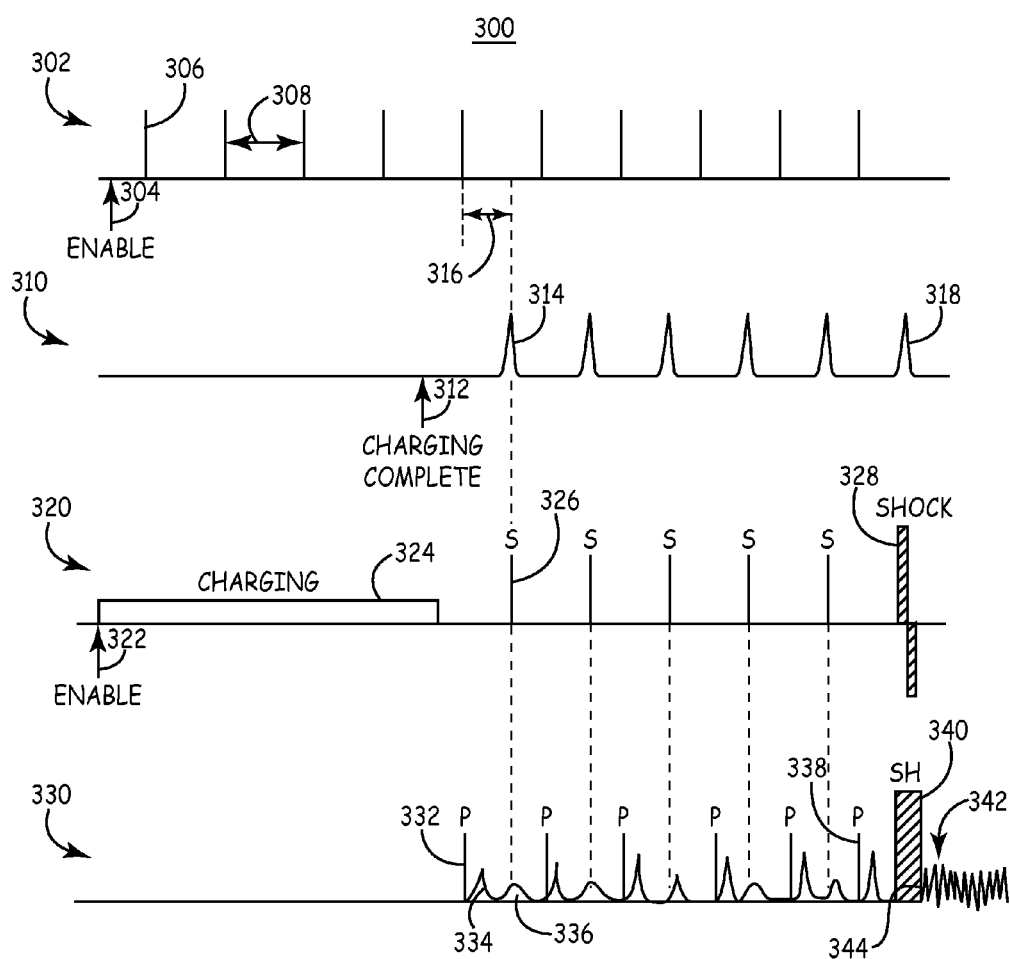
FIG. 3 is a timing diagram illustrating a sequence of events according to one embodiment of the invention for controlling the delivery of an externally-generated shock pulse for inducing fibrillation.

FIG. 3 is a timing diagram 300 illustrating a sequence of events according to one embodiment of the invention for controlling the delivery of an external shock pulse for inducing fibrillation. Timeline 302 represents the output of external pacing source 102 coupled to induction interface 100. At 304, external pacing source 102 is enabled to deliver pacing pulses 306 at a desired pulse interval 308. Pacing source 102 may be enabled at 304 directly by a user or indirectly by a user entering an induction command on induction interface 100.

Timeline 310 represents output of induction interface 100. Upon receiving a charging complete signal 312, induction interface 100 generates a series of QRS signals 314. Each QRS signal 314 is generated at a time delay 316 following a pacing pulse 306 received from external pacing source 102. Induction interface 100 may be configured to deliver a specified number of QRS signals, for example 6 to 8 QRS signals, used by external shock source 104 for synchronizing a shock pulse.

Timeline 320 represents the events relating to external shock source 104. At 322, external shock source is enabled to begin capacitor charging 324. Upon completion of charging 324, the charging complete signal 312 is provided to induction interface 310. External shock source may be enabled to begin charging directly by a user or indirectly by a user using induction interface 100. The charging complete signal 312 may be provided to induction interface 100 automatically by the external shock source or may be applied by a user observing a charge indicator on the external shock source 104.

External shock source 104 receives the QRS signals 314 generated by induction interface 100, which are recognized by sensing circuitry in external shock source 104 as sensed events 326. A shock pulse 328 is synchronized to the last QRS signal 318, occurring during the T-wave 344. The number of QRS signals 314 generated by induction interface 100 and sensed by external shock source 104 prior to delivering shock pulse 328 may vary between embodiments and may in part depend on the synchronization algorithm used by the shock source 104 for synchronizing a shock pulse with a sensed event.

Timeline 330 represents output received by the patient from induction interface 100. Once charging 324 is complete, induction interface 100 passes pacing pulses 306 generated by external pacing source 102 to the patient, shown as pacing pulses 332 on timeline 330. Each pacing pulse 332 is delivered with a pulse energy expected to successfully capture the patient's heart. As such, an evoked QRS signal 334 and subsequent T-wave 336 is shown following each pacing pulse. QRS signals 314 are generated by induction interface 100 at a time delay 316 which is expected to correspond to the time of T-wave 336 following each pacing pulse. Following the last pacing pulse 338, the shock pulse 328 generated by external shock source 104 is modulated as desired and delivered to the patient, shown as shock pulse 340. Shock 340 is delivered, at a time that corresponds to a T-wave 344 following the last delivered pacing pulse 338. Shock pulse 328 generated by shock source 104 is shown as biphasic shock. Shock pulse 328 is modified by induction interface 100 to produce the prolonged, monophasic shock pulse 340 actually delivered to the patient. The prolonged, monophasic shock pulse is expected to be more effective in inducing fibrillation than the biphasic pulse 328 generated by the external shock source and typically used for defibrillation rather than fibrillation induction.

A shock pulse having adequate energy below the patient's upper limit of vulnerability and appropriately timed relative to the patient's vulnerable period will induce ventricular fibrillation 342. During an implant procedure, an implantable defibrillator will detect the induced fibrillation 342 and attempt to deliver a shock pulse to terminate the induced fibrillation 342. In this way, defibrillation threshold tests can be performed using an implantable defibrillator that is not capable of reliably inducing fibrillation.

In FIG. 3, the number of pacing pulses 332 passed to the patient by induction interface 300 is equal to the number of generated QRS signals 314 received by external shock source 104 and used in synchronizing shock pulse 328. However, in other embodiments, the number of pacing pulses 332 passed to the patient may be different than the number of QRS signals 313 received by external shock source 104. For example, it is typically desirable to deliver 6 to 8 pacing pulses during T-wave shock delivery in order to establish a stable cardiac rhythm and thereby promote accurate timing of the shock pulse during the T-wave. However, external shock source 104 may synchronize a shock pulse to the next QRS signal sensed after charging is complete. As such, in one embodiment, only one QRS signal 318 may be generated by induction interface 100 following the last pacing pulse 338 of a series of pacing pulses 332 delivered to the patient.

Furthermore it is recognized that QRS signals 314 may be applied to external shock source 104 during charging 324 and pacing pulses 306 generated by external passing source 102 may already be passed to the patient during charging 324 such that the last pacing pulse 338 and subsequent QRS signal 318 for synchronizing shock pulse 328 occur earlier after completion of capacitor charging at 312.

While embodiments described herein have illustrated the use of induction interface in inducing ventricular fibrillation, for example for use in determining a defibrillation threshold, the induction system and methods described may be used in any application requiring an external shock to be delivered at a particular time in the cardiac cycle. For example, the induction interface system and methods described herein may be used during upper limit of vulnerability (ULV) testing. ULV testing is performed to determine the patient's ULV for estimating the defibrillation threshold or verifying that an ICD shock output capacity is at least a safety margin above the patient's defibrillation threshold. During ULV testing, a properly timed T-wave shock will not actually induce fibrillation if the shock strength is above the patient's ULV. As such, it is recognized that practice of the present invention is not limited to delivery of shock pulses intended to induce fibrillation.

Thus, a method and apparatus for synchronizing externally applied shock pulses to a patient's cardiac cycle have been presented in the foregoing description with reference to specific embodiments. It is appreciated that various modifications to the referenced embodiments may be made without departing from the scope of the invention as set forth in the following claims.

The invention claimed is:

1. An apparatus for delivering an external shock pulse, comprising:
 a first input for receiving pacing pulses from a first device enabled to deliver the pacing pulses at a pulse energy;
 a second input for receiving a shock pulse from a second device;
 an output for coupling the apparatus to electrodes coupled to a patient;
 a pacing control for controlling delivery of the received pacing pulses to the output;
 a shock control for controlling delivery of the received shock pulse to the output; and
 a control module coupled to the pacing control and the shock control;
 the control module, the pacing control and the shock control configured to cooperatively control delivery of the received shock pulse to the output at a predetermined delay after one of the received pacing pulses.

2. The apparatus of claim 1 wherein the pacing control comprises an impedance load coupled to the first device via the first input.

3. The apparatus of claim 1 wherein the pacing control being configured to electrically uncouple the first input from first device prior to the shock pulse being delivered.

4. The apparatus of claim 1 wherein the control module is configured to receive a charge signal from the second device and the pacing control being configured to pass received pacing pulses to the output in response to the charge signal.

5. The apparatus of claim 4 wherein the pacing control being configured to withhold the received pacing pulses from the output when the charge signal has not reached a charge threshold.

6. The apparatus of claim 1 further comprising an output coupled to the second device wherein the shock control configured to generate a simulated QRS signal at the predetermined time delay after the received pacing pulses, the QRS signal transferred to the second device via the output.

7. The apparatus of claim 6 wherein the predetermined time delay corresponds to a Q-T interval of the patient.

8. The apparatus of claim 7 wherein the shock control comprises a shock modulation circuit to modulate a waveform of the shock pulse.

9. The apparatus of claim 8 wherein the received shock pulse waveform being a biphasic waveform and the shock modulation circuit comprising a rectifier to modulate the biphasic waveform to be a monophasic waveform.

10. The apparatus of claim 9 wherein the shock modulation circuit further comprising circuitry for prolonging the monophasic waveform.

11. The apparatus of claim 1 further comprising a user interface coupled to the control module for receiving user input, the user input comprising at least one of a start button to initiate the shock pulse delivery; a shock energy selector for controlling the energy of the shock pulse passed to the output, and a delay selector for selecting the predetermined time delay.

12. The apparatus of claim 5, further comprising:
a dissipative circuit; and
the pacing control selectively passing the received pacing pulses to the dissipative circuit to withhold the received pacing pulses from the output.

* * * * *